(12) United States Patent
Yu et al.

(10) Patent No.: US 12,240,888 B1
(45) Date of Patent: Mar. 4, 2025

(54) COMPOSITION COMPRISING AFLIBERCEPT AND A VARIANT THEREOF, AND RELATED METHODS AND USES

(71) Applicant: QILU PHARMACEUTICAL CO., LTD., Shandong (CN)

(72) Inventors: Yue Yu, Shandong (CN); Guijiang Wang, Shandong (CN); Jiulin Wang, Shandong (CN); Zhenming An, Shandong (CN); Qingmin Wang, Shandong (CN); Daoyuan Li, Shandong (CN); Chuanlei Liu, Shandong (CN); Feifei Liu, Shandong (CN); Huanlan Zheng, Shandong (CN); Peng Wan, Shandong (CN); Bo Xie, Shandong (CN)

(73) Assignee: QILU Pharmaceutical, Co., Ltd., Shandong (CN)

( * ) Notice: Subject to any disclaimer, the term of this patent is extended or adjusted under 35 U.S.C. 154(b) by 0 days.

(21) Appl. No.: 18/679,192

(22) Filed: May 30, 2024

(30) Foreign Application Priority Data

Apr. 29, 2024 (CN) .......................... 202410533566.4

(51) Int. Cl.
- *C07K 14/71* (2006.01)
- *C12Q 1/37* (2006.01)
- *G01N 33/68* (2006.01)

(52) U.S. Cl.
CPC ................ *C07K 14/71* (2013.01); *C12Q 1/37* (2013.01); *G01N 33/6848* (2013.01); *C07K 2319/30* (2013.01); *G01N 2333/71* (2013.01); *G01N 2333/976* (2013.01)

(58) Field of Classification Search
CPC ...... C07K 14/71; C07K 2319/30; C12Q 1/37; G01N 33/6848; G01N 2333/71; G01N 2333/976
See application file for complete search history.

(56) References Cited

U.S. PATENT DOCUMENTS

| | | | |
|---|---|---|---|
| 7,070,959 B1 | 7/2006 | Papadopoulos et al. | |
| 7,635,474 B2 | 12/2009 | Daly et al. | |
| 9,511,140 B2 | 12/2016 | Dix et al. | |
| 11,053,280 B2 | 7/2021 | Tustian et al. | |
| 11,084,865 B2 | 8/2021 | Furfine et al. | |
| 11,186,625 B2 | 11/2021 | Wang et al. | |
| 11,505,593 B2 | 11/2022 | Wang et al. | |
| 12,054,532 B2 | 8/2024 | Wang et al. | |
| 2011/0305694 A1* | 12/2011 | Hamblin | A61P 29/00 435/254.2 |
| 2012/0070436 A1* | 3/2012 | Easeman | C07K 16/32 435/254.2 |
| 2014/0186350 A1* | 7/2014 | Ghosh | A61K 31/713 424/134.1 |
| 2020/0231665 A1* | 7/2020 | Karow | C07K 16/2803 |
| 2020/0338164 A1 | 10/2020 | Wexler-Cohen et al. | |
| 2022/0098279 A1 | 3/2022 | Luo et al. | |

FOREIGN PATENT DOCUMENTS

CN 105175548 A1 12/2015

OTHER PUBLICATIONS

Jackson A long-acting anti-VEGF biologic in development for durable wet-age-related macular degeneration (AMD) Investigative Ophthalmology & Visual Science (IVOS) ARVO Annual Meeting Abstract Jun. 2023 (Year: 2023).*
European Search Report dated Dec. 2, 2024 in related European Application No. 24180422.8; twelve pages.

* cited by examiner

*Primary Examiner* — Changhwa J Cheu
(74) *Attorney, Agent, or Firm* — Kilpatrick Townsend & Stockton LLP

(57) ABSTRACT

Provided is a composition comprising aflibercept and a variant thereof, wherein the variant is a truncation variant with a truncated VEGF binding portion of aflibercept, and wherein the content of the truncation variant is less than or equal to about 20% by mass percentage. Also provided is a pharmaceutical formulation comprising the composition. Further, provided are a method for detecting the variant and use of the variant in quality inspection or quality control of an aflibercept-containing product.

5 Claims, 3 Drawing Sheets

Specification includes a Sequence Listing.

Sequence of a first peptide chain (SEQ ID NO: 1)

Sequence of a second peptide chain is the same as that of the first peptide chain

SEQUENCE LISTING

```
Sequence total quantity: 4
SEQ ID NO: 1            moltype = AA  length = 432
FEATURE                 Location/Qualifiers
source                  1..432
                        mol_type = protein
                        organism = synthetic construct
SEQUENCE: 1
SDTGRPFVEM YSEIPEIIHM TEGRELVIPC RVTSPNITVT LKKFPLDTLI PDGKRIIWDS   60
RKGFIISNAT YKEIGLLTCE ATVNGHLYKT NYLTHRQTNT IIDVVLSPSH GIELSVGEKL  120
VLNCTARTEL NVGIDFNWEY PSSKHQHKKL VNRDLKTQSG SEMKKFLSTL TIDGVTRSDQ  180
GLYTCAASSG LMTKKNSTFV RVHEKDKTHT CPPCPAPELL GGPSVFLFPP KPKDTLMISR  240
TPEVTCVVVD VSHEDPEVKF NWYVDGVEVH NAKTKPREEQ YNSTYRVVSV LTVLHQDWLN  300
GKEYKCKVSN KALPAPIEKT ISKAKGQPRE PQVYTLPPSR DELTKNQVSL TCLVKGFYPS  360
DIAVEWESNG QPENNYKTTP PVLDSDGSFF LYSKLTVDKS RWQQGNVFSC SVMHEALHNH  420
YTQKSLSLSP GK                                                     432

SEQ ID NO: 2            moltype = AA  length = 333
FEATURE                 Location/Qualifiers
source                  1..333
                        mol_type = protein
                        organism = synthetic construct
SEQUENCE: 2
TIIDVVLSPS HGIELSVGEK LVLNCTARTE LNVGIDFNWE YPSSKHQHKK LVNRDLKTQS   60
GSEMKKFLST LTIDGVTRSD QGLYTCAASS GLMTKKNSTF VRVHEKDKTH TCPPCPAPEL  120
LGGPSVFLFP PKPKDTLMIS RTPEVTCVVV DVSHEDPEVK FNWYVDGVEV HNAKTKPREE  180
QYNSTYRVVS VLTVLHQDWL NGKEYKCKVS NKALPAPIEK TISKAKGQPR EPQVYTLPPS  240
RDELTKNQVS LTCLVKGFYP SDIAVEWESN GQPENNYKTT PPVLDSDGSF FLYSKLTVDK  300
SRWQQGNVFS CSVMHEALHN HYTQKSLSLS PGK                               333

SEQ ID NO: 3            moltype = AA  length = 432
FEATURE                 Location/Qualifiers
source                  1..432
                        mol_type = protein
                        organism = synthetic construct
SEQUENCE: 3
SDTGRPFVEM YSEIPEIIHM TEGRELVIPC RVTSPNITVT LKKFPLDTLI PDGKRIIWDS   60
RKGFIISNAT YKEIGLLTCE ATVNGHLYKT NYLTHRQTNT IIDVVLSPSH GIELSVGEKL  120
```

```
VLNCTARTEL NVGIDFNWEY PSSKHQHKKL VNRDLKTQSG SEMKKFLSTL TIDGVTRSDQ    180
GLYTCAASSG LMTKKNSTFV RVHEKDKTHT CPPCPAPELL GGPSVFLFPP KPKDTLMISR    240
TPEVTCVVVD VSHEDPEVKF NWYVDGVEVH NAKTKPREEQ YNSTYRVVSV LTVLHQDWLN    300
GKEYKCKVSN KALPAPIEKT ISKAKGQPRE PQVYTLPPCR DELTKNQVSL WCLVKGFYPS    360
DIAVEWESNG QPENNYKTTP PVLDSDGSFF LYSKLTVDKS RWQQGNVFSC SVMHEALHNH    420
YTQKSLSLSP GK                                                       432

SEQ ID NO: 4           moltype = AA  length = 333
FEATURE                Location/Qualifiers
source                 1..333
                       mol_type = protein
                       organism = synthetic construct
SEQUENCE: 4
TIIDVVLSPS HGIELSVGEK LVLNCTARTE LNVGIDFNWE YPSSKHQHKK LVNRDLKTQS     60
GSEMKKFLST LTIDGVTRSD QGLYTCAASS GLMTKKNSTF VRVHEKDKTH TCPPCPAPEL    120
LGGPSVFLFP PKPKDTLMIS RTPEVTCVVV DVSHEDPEVK FNWYVDGVEV HNAKTKPREE    180
QYNSTYRVVS VLTVLHQDWL NGKEYKCKVS NKALPAPIEK TISKAKGQPR EPQVCTLPPS    240
RDELTKNQVS LSCAVKGFYP SDIAVEWESN GQPENNYKTT PPVLDSDGSF FLVSKLTVDK    300
SRWQQGNVFS CSVMHEALHN RYTQKSLSLS PGK                                 333
```

US 12,240,888 B1

COMPOSITION COMPRISING AFLIBERCEPT AND A VARIANT THEREOF, AND RELATED METHODS AND USES

REFERENCE TO AN ELECTRONIC SEQUENCE LISTING

The contents of the electronic sequence listing (24C10812-Sequencelisting.xml; Size: 5,9111 bytes; and Date of Creation: May 29, 2024) is herein incorporated by reference in its entirety.

TECHNICAL FIELD

The present application relates to the field of pharmaceutical formulations. In particular, the present application provides a composition comprising aflibercept and a variant thereof, as well as related methods and uses.

BACKGROUND OF THE INVENTION

Vascular endothelial growth factor (VEGF) is the most classical angiogenic factor in a human body, which can promote angiogenesis and enhance vascular permeability. VEGF abnormalities can lead to a variety of ocular diseases including wet age-related macular degeneration (wet-AMD) and diabetic retinopathy (DR).

Aflibercept is an inhibitor of VEGF, which is a recombinant fusion protein derived from the fusion of the Fc portion of human IgG1 immunoglobulin with a VEGF binding portion from extracellular domains of human VEGF receptors 1 and 2. Aflibercept has been shown to be effective in preventing neovascularization of CoNV. It has been approved for the treatment of wet macular degeneration in the United States and Europe (under the trade name Eylea™).

As a medicine, aflibercept must maintain its stability and efficacy. The quality control of a pharmaceutical composition is mainly concerned with the control of the contents of active ingredients and related substances such as variants or impurities. In particular, the contents of the related substances need to meet the medicinal requirements.

SUMMARY OF THE INVENTION

In a first aspect, the present application provides a composition comprising aflibercept and a variant thereof, wherein the variant is a truncation variant with a truncated VEGF binding portion of aflibercept, and comprises a first peptide chain with an amino acid sequence set forth in SEQ ID NO: 1 and a second peptide chain with an amino acid sequence set forth in SEQ ID NO: 2, and wherein the content of the truncation variant is less than or equal to about 20% by mass percentage.

In particular embodiments, the content of the truncation variant is less than or equal to about 20%, which is calculated based on a trypsin-cleaved peptide mass fingerprinting analysis.

In some embodiments, the content of aflibercept in the composition is greater than or equal to about 80%, calculated as a mass percentage, e.g., based on a trypsin-cleaved peptide mass fingerprinting analysis.

In some embodiments, the content of the truncation variant in the composition is greater than or equal to about 0.01%, greater than or equal to about 0.05%, greater than or equal to about 0.1%, greater than or equal to about 0.5%, greater than or equal to about 1%, greater than or equal to about 1.5%, or greater than or equal to about 2%, calculated as a mass percentage, e.g., based on a trypsin-cleaved peptide mass fingerprinting analysis.

In some embodiments, the content of the truncation variant in the composition is less than or equal to about 19%, less than or equal to about 18%, less than or equal to about 17%, less than or equal to about 16%, less than or equal to about 15%, less than or equal to about 14%, less than or equal to about 13%, less than or equal to about 12%, less than or equal to about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 2.5%, less than or equal to about 2%, less than or equal to about 1.5%, less than or equal to about 1%, less than or equal to about 0.9%, less than or equal to about 0.8%, less than or equal to about 0.7%, less than or equal to about 0.6%, less than or equal to about 0.5%, less than or equal to about 0.4%, less than or equal to about 0.3%, less than or equal to about 0.2%, or less than or equal to about 0.1%, calculated as a mass percentage, e.g., based on a trypsin-cleaved peptide mass fingerprinting analysis. In some embodiments, the content of the truncation variant may be any interval within the range defined by any two of the above-mentioned values, or any value within the interval.

The truncation variant, also referred to herein as T100, will be described in detail below.

In a second aspect, the present application provides a pharmaceutical formulation comprising the composition disclosed in the first aspect, and one or more pharmaceutically acceptable carriers.

In a third aspect, the present application provides a method of preparing the pharmaceutical formulation disclosed in the second aspect, comprising the steps of:

(1) preparing a composition comprising aflibercept and a variant thereof, wherein the variant is the truncation variant as defined in the first aspect above, and (2) evaluating the truncation variant in the composition, and confirming the content of the truncation variant is less than or equal to about 20%.

In some embodiments, the above step (2) includes subjecting the composition to a peptide mass fingerprinting analysis to obtain XIC chromatograms of a truncated peptide segment and a full-length peptide segment, and calculating the content of the truncation variant from corresponding peak areas.

In some embodiments, the method further comprises combining the composition obtained after the above step (2) with a pharmaceutically acceptable carrier.

In a fourth aspect, the present application provides a method of detecting a variant of aflibercept in an aflibercept-containing composition or pharmaceutical formulation, wherein the variant is a truncation variant with a truncated VEGF binding portion of aflibercept, and comprises a first peptide chain with an amino acid sequence set forth in SEQ ID NO: 1 and a second peptide chain with an amino acid sequence set forth in SEQ ID NO: 2, and wherein the method comprises:

subjecting the composition or pharmaceutical formulation to a subunit molecular weight analysis, for example, by using LC-MS, after being cleaved with an IdeS enzyme, and determining the presence or absence of the variant based on molecular weight; or subjecting the composition or pharmaceutical formulation to a peptide mass fingerprinting analysis, for example, by using LC-MS/MS, after being cleaved with a trypsin, and determining the presence or absence of the variant based on the first-order and second-order mass spectra.

In some embodiments, when the presence of the variant is determined by the peptide mass fingerprinting analysis after trypsin cleavage, the method further comprises obtaining XIC chromatograms of a truncated peptide segment and a full-length peptide segment after the peptide mass fingerprinting analysis, and calculating the content of the truncation variant from corresponding peak areas.

In a fifth aspect, the present application provides a method for quality inspection or quality control of an aflibercept-containing product, comprising detecting the content of a variant of aflibercept in the aflibercept-containing product, wherein the variant is the truncation variant as defined in the first aspect. In some embodiments, the aflibercept-containing product is the composition disclosed in the first aspect or the pharmaceutical formulation disclosed in the second aspect.

In some embodiments, if the content of the variant is detected to be less than or equal to about 20%, the aflibercept-containing product meets the medicinal requirements.

In a sixth aspect, the present application provides use of a variant of aflibercept, which is the truncation variant as defined in the first aspect, in a quality inspection or quality control of an aflibercept-containing product. In some embodiments, the aflibercept-containing product is the composition disclosed in the first aspect or the pharmaceutical formulation disclosed in the second aspect.

DESCRIPTION OF THE SEQUENCES

Figure 1:
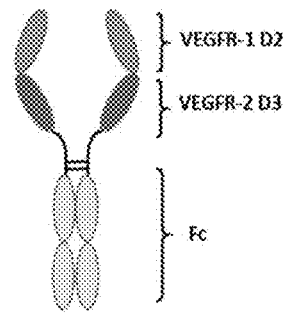
FIG. 1 shows the sequence and structure of aflibercept.

SEQ ID NO:1 is the amino acid sequence of two identical peptide chains of aflibercept and is shown as below (Note: the bold part is the VEGFR-1 D2 domain, the underlined part is the VEGFR-2 D3 domain, and the italic part is the Fc segment):

SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDENWEYPSSKHQHKKL

VNRDLKTQSGSEMKKFLSTLTIDGVTRSDQGLYTCAASSGLMTKKNSTFV

RVHEKDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

SEQ ID NO:2 is a truncated sequence of SEQ ID NO:1 in which 99 amino acid residues at the N-terminus are deleted. The specific sequence is shown as below (Note: the bold part is the VEGFR-1 D2 domain, the underlined part is the VEGFR-2 D3 domain, and the italic part is the Fc segment):

TIIDVVLSPSHGIELSVGEKLVLNCTARTELNVGIDFNWEYPSSKHQHKK

LVNRDLKTQSGSEMKKFLSTLTIDGVTRSDQGLYTCAASSGLMTKKNSTF

VRVHEKDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGK

SEQ ID NO:3 is the amino acid sequence of the longer peptide chain in the T100 sequence for recombinant expression and is shown as follows (Note: the residues shown in italics are mutated amino acids):

SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDENWEYPSSKHQHKKL

VNRDLKTQSGSEMKKFLSTLTIDGVTRSDQGLYTCAASSGLMTKKNSTFV

RVHEKDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPP*C*RDELTKNQVSL

*W*CLVKGFYPSDIAVEWESNGQPENNYKTTPPVLDSDGSFFLYSKLTVDKS

R*W*QQGNVFSCSVMHEALHNHYTQKSLSLSPGK

SEQ ID NO:4 is the amino acid sequence of the shorter peptide chain in the T100 sequence for recombinant expression and is shown as below (Note: the residues shown in italics are mutated amino acids):

TIIDVVLSPSHGIELSVGEKLVLNCTARTELNVGIDFNWEYPSSKHQHKK

LVNRDLKTQSGSEMKKFLSTLTIDGVTRSDQGLYTCAASSGLMTKKNSTF

VRVHEKDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQV*C*TLPP*S*RDELTKNQVS

L*S*CAVKGFYPSDIAVEWESNGQPENNYKTTPPVLDSDGSFFL*V*SKLTVDK

SRWQQGNVFSCSVMHEALHN*R*YTQKSLSLSPGK

DETAILED DESCRIPTION

Angiogenesis is essential for the development of blood vessels in normal embryos and postnatal subjects. Abnormal or pathological angiogenesis is a marker of cancers and several retinal diseases in which upregulation of pro-angiogenic factors (such as vascular endothelial growth factor (VEGF)) leads to increased endothelial growth, morphological changes in the vasculature, and increased vascular permeability. Elevated levels of VEGF are found in both vitreous humor and retinal vasculature in patients suffering from various eye diseases. The blockade of VEGF activity has become the preferred treatment for ocular diseases such as DME, wet AMD, CNV, and retinal vein occlusion.

Aflibercept is an anti-VEGF protein, which is a homodimer formed from two identical peptide chains linked by disulfide bonds, comprising a human amino acid sequence which comprises the second Ig domain of human VEGFR-1 (VEGFR-1 D2) and the third Ig domain of human VEGFR-2 (VEGFR-2 D3). In particular embodiments, the sequence of the two identical peptide chains of aflibercept is shown in SEQ ID NO: 1.

The inventors of the present application have surprisingly found that a variant of aflibercept, for example one with a truncation of its peptide chain, was generated during the preparation of aflibercept. The variant does not affect the binding activity and biological activity of an aflibercept sample, if its content is less than or equal to about 20%. In other words, as long as the content of the variant of aflibercept does not exceed about 20%, the binding activity of aflibercept to VEGF and the biological activity of aflibercept do not decrease. Therefore, during the preparation of aflibercept, if the variant of aflibercept is evaluated to be in an amount of no higher than 20%, there is no need to carry out the operation of removing the variant or impurity. This will simplify the production process and reduce the production cost to a certain extent.

In some embodiments, commercially available Eylea™ is used as a positive control to detect relevant activities of a composition comprising aflibercept and a variant thereof, including the binding activity to VEGF and biological activities such as, inhibition of proliferation of HUVEC cells.

In some embodiments, the biological activity of aflibercept in the composition disclosed herein is determined by a VEGF activity neutralization-HUVEC cell proliferation inhibition assay.

In particular embodiments, the inventors have identified the above variant and found that it differs from aflibercept only in that 99 amino acid residues at the N-terminus of one of the two peptide chains are deleted, where the other peptide chain is identical to SEQ ID NO: 1. Sequence of the truncated peptide chain is shown in SEQ ID NO: 2. As the truncated peptide chain starts from threonine at position 100 of SEQ ID NO: 1, this variant is designated herein as "T100".

In some embodiments, in the composition comprising aflibercept and a variant thereof disclosed herein, the variant of aflibercept is T100, wherein the content of the variant T100 does not exceed 20%.

In some embodiments, the composition disclosed herein consists of aflibercept and a variant thereof (e.g., T100).

Described herein is the use of a cell culture medium to prepare aflibercept. In some embodiments, the cell culture medium is a chemically defined medium ("CDM").

In particular embodiments, the cell culture medium used herein contains the following main components: 4-hydroxyethylpiperazine ethane sulfonic acid, glucose, sodium pyruvate, sodium chloride, potassium chloride, sodium selenite, manganese sulfate, ethanolamine, iron citrate, zinc sulfate, copper sulfate, glutathione, magnesium chloride, sodium dihydrogen phosphate, sodium bicarbonate, alanine, asparagine, arginine, aspartic acid, cystine, cysteine, glutamic acid, glycine, histidine, isoleucine, leucine, lysine, methionine, phenylalanine, proline, serine, threonine, tryptophan, tyrosine, valine, biotin, calcium pantothenate, choline chloride, folic acid, inositol, nicotinamide, vitamin B6, vitamin B2, vitamin B1, vitamin B12, linoleic acid, blocked polyether F-68, and yeast extract.

In some embodiments, aflibercept is expressed in a suitable host cell. Non-limiting examples of such host cell include, but are not limited to, CHO, CHO K1, NS0, Sp2/0, embryonic kidney cells, BHK, and the like.

In some embodiments, the process for purifying aflibercept comprises one or more steps selected from affinity chromatography, anion exchange chromatography, cation exchange chromatography, hydrophobic chromatography, desalination chromatography, virus removal nanofiltration, and ultrafiltration concentration.

In some embodiments, an aflibercept sample is subjected to a molecular weight analysis of IdeS-cleaved non-reducing subunits. In particular embodiments, after the IdeS cleavage ends, the sample to be tested is subjected to the subunit molecular weight analysis by using liquid chromatography-mass spectrometry (LC-MS).

In the present application, the inventors have surprisingly discovered the variant T100 in the course of the subunit molecular weight analysis of the IdeS-cleaved aflibercept sample by LC-MS.

In some embodiments, the variant T100 in an aflibercept product may be reduced or removed by ion exchange chromatography, hydrophobic chromatography, composite chromatography, etc.

In some embodiments, liquid chromatography-tandem mass spectrometry (LC-MS/MS) analysis is used to detect the variant T100 in an aflibercept product. For example, the sample to be tested may be subjected to a peptide mass fingerprinting analysis by LC-MS/MS.

In particular embodiments, after the mass spectrometry data are obtained, extracted ion chromatograms (XIC) of two charge forms which have the strongest responses to the truncated peptide segment and its corresponding full-length peptide segment are extracted, and integrated to obtain respective peak areas. The content of T100 is calculated according to the following formula:

$$\text{The content of } T100 = \frac{XIC \text{ area of truncated peptide segment}}{XIC \text{ area of truncated peptide segment} + XIC \text{ area of full-length peptide segment}} \times 100\%$$

In some embodiments, the inventors of the present application have surprisingly found that the content of the variant T100 is less than or equal to about 20% in a prepared sample of aflibercept without diminishing the binding activity of aflibercept to VEGF.

In some embodiments, the inventors of the present application have surprisingly found that the content of the variant T100 is less than or equal to about 20% in a prepared sample of aflibercept without reducing the biological activity of aflibercept.

In some embodiments, the content of a variant (e.g., T100) in the composition comprising aflibercept and a variant thereof disclosed herein is about 0.01%-about 20%, about 0.05%-about 20%, about 0.1%-about 20%, about 0.2%-about 20%, about 0.3%-about 20%, about 0.4%-about 20%, about 0.5%-about 20%, about 0.6%-about 20%, about 0.7%-about 20%, about 0.8%-about 20%, about 0.9%-about 20%, about 1%-about 20%, about 1.5%-about 20%, about 2%-about 20%, about 2.5%-about 20%, about 3%-about 20%, about 3.5%-about 20%, about 4%-about 20%, about 4.5%-about 20%, about 5%-about 20%, about 5.5%-about 20%, about 6%-about 20%, about 6.5%-about 20%, about 7%-about 20%, about 7.5%-about 20%, about 8%-about 20%, about 8.5%-about 20%, about 9%-about 20%, about 9.5%-about 20%, about 10%-about 20%, about 11%-about 20%, about 12%-about 20%, about 13%-about 20%, about 14%-about 20%, about 15%-about 20%, about 16%-about 20%, about 17%-about 20%, about 18%-about 20%, about 19%-about 20%, or any interval within any of the above ranges or any value within the interval.

In particular embodiments, the content of a variant (e.g., T100) in the composition comprising aflibercept and a variant thereof disclosed herein is about 0.5%-about 10%, about 0.5%-about 9%, about 0.5%-about 8%, about 0.5%-about 7%, about 0.5%-about 6%, about 0.5%-about 5%, about 0.5%-about 4%, about 0.5%-about 3%, about 0.5%-about 2%, about 0.5%-about 1%, or any interval within any of the above ranges or any value within the interval. For example, the content of a variant (e.g., T100) is 0.86%-19.29%, preferably 0.86%-2.59%.

Also disclosed herein is the preparation of a pharmaceutical formulation of the composition disclosed herein, i.e., mixing the composition with optional pharmaceutically acceptable carriers, and storing in a lyophilized formulation or an aqueous solution. The pharmaceutically acceptable carriers are non-toxic to a recipient at the dosages and concentrations employed. In some embodiments, the pharmaceutically acceptable carriers include, for example, water; buffers such as phosphates, citrates and other organic acids; antioxidants such as ascorbic acid and methionine; preservatives; hydrophilic polymers such as polyvinylpyrrolidone; and chelating agents such as EDTA. In some embodiments, formulations for in vivo administration must be sterilized, which can be easily achieved by filtration with a sterile filtration membrane.

In this specification and in the claims, the term "about" refers to a numerical range considered by one of ordinary skill in the art to be equivalent to the recited numerical value (e.g., having the same function or result), e.g., +/−10% of the recited numerical value.

In this specification and in the claims, the phrases "include", "comprise" and "contain" mean "include but are not limited to", and does not intended to exclude other parts, additives, components or steps.

It should be understood that features, characteristics, components, or steps described in a particular aspect, embodiment, or example of the present application can be applied to any other aspect, embodiment, or example described herein unless contradicted thereby.

The above disclosure generally describes the present invention, which will be further exemplified by the following Examples. These Examples are described merely to illustrate the invention and are not intended to limit the scope of the invention. Although specific terms and values are used herein, such terms and values are also understood to be exemplary and do not limit the scope of the invention. Unless otherwise specified, the experimental methods and techniques in this specification are those well known to a person skilled in the art.

EXAMPLES

Example 1 Preparation of Aflibercept

Upstream Cell Culture Process

The expression system employed in this Example was the Freedom™ CHO-STM Kit from Thermo Fisher Scientific, which included a CHO-S host cell line and pCHO1.0 expression plasmid for cGMP library construction. The expression vector was pCHO1.0 plasmid that enabled efficient expression of exogenous recombinant proteins in mammal cells. The production medium contained the following main components: 4-hydroxyethylpiperazine ethane sulfonic acid, glucose, sodium pyruvate, sodium chloride, potassium chloride, sodium selenite, manganese sulfate, ethanolamine, iron citrate, zinc sulfate, copper sulfate, glutathione, magnesium chloride, sodium dihydrogen phosphate, sodium bicarbonate, alanine, asparagine, arginine, aspartic acid, cystine, cysteine, glutamic acid, glycine, histidine, isoleucine, leucine, lysine, methionine, phenylalanine, proline, serine, threonine, tryptophan, tyrosine, valine, biotin, calcium pantothenate, choline chloride, folic acid, inositol, nicotinamide, vitamin B6, vitamin B2, vitamin B1, vitamin B12, linoleic acid, blocked polyether F-68, and yeast extract.

In accordance with typical cell culture processes of antibody drugs, the production of a stock solution of aflibercept was carried out according to a process of cell recovery, step-by-step expansion in a shake flask and a bioreactor, and production in a production tank, in which a feeding batch culture process was used in the production stage.

Cells in a cell cryopreservation tube were thawed in a water bath at 37° C., cultured in a shake-flask expansion medium, successively expanded in a shake flask and a bioreactor, and inoculated into the production tank for production.

In accordance with typical cell culture processes of antibody drugs, suitable process parameters such as culture temperature, pH, dissolved oxygen, stirring speed, and ventilation were set at the production stage, an appropriate feeding medium and glucose solution were added according to requirements for cell growth, and a solution of antifoaming agent was added according to requirements for culture. After the end of culturing, cell culture was subjected to deep filtration and sterilization by filtration. Supernatant was collected for purification.

Downstream Purification Process

In accordance with typical cell culture processes of antibody drugs, this Example included affinity chromatography, anion exchange chromatography, cation exchange chromatography, hydrophobic chromatography, desalination chromatography, virus removal nanofiltration, and ultrafiltration concentration, so as to finally obtain a stock solution of the target protein.

Affinity chromatography. After equilibration of the affinity chromatography column with a salt-containing buffer (the salt was selected from $Na_2SO_4$, NaCl or $(NH_4)_2SO_4$), the loading phase initiated. After the end of the loading, the salt-containing buffer was further used for washing, followed by washing with a salt-free buffer. Elution was performed with a buffer at pH 3.0-4.5. A solution of the eluted protein was collected and then subjected to viral inactivation.

Anion exchange chromatography. The anion exchange chromatography column was pre-equilibrated with a salt-containing buffer (the salt was selected from $Na_2SO_4$, NaCl or $(NH_4)_2SO_4$), equilibrated with a salt-free buffer, and loaded with the protein solution obtained after the viral inactivation. After the end of the loading, the salt-free equilibration buffer was further used for washing, followed by washing with an equilibration buffer containing 0.02-0.06 mol/L of salt. Elution was performed with a buffer containing 0.1-0.2 mol/L of salt, so as to elute the protein from the anion exchange chromatography column. A solution of the eluted protein was collected.

Cation exchange chromatography. The cation exchange chromatography column was pre-equilibrated with a salt-containing buffer (the salt was selected from $Na_2SO_4$, NaCl or $(NH_4)_2SO_4$), then equilibrated with a salt-free buffer, and loaded with the protein solution collected from anion exchange chromatography. After the end of the loading, the salt-free equilibration buffer was further used for washing, and then an equilibration buffer containing 0.1-0.2 mol/L of salt was used for elution, so as to elute the protein from the cation exchange chromatography column. A solution of the eluted protein was collected.

Hydrophobic chromatography. The hydrophobic chromatography column was equilibrated with a salt-containing buffer (the salt was selected from $Na_2SO_4$, NaCl or $(NH_4)_2SO_4$), and loaded with the protein solution collected from cation exchange chromatography. After the end of the loading, the salt-containing equilibration buffer was further used for washing, and then an equilibration buffer containing 0.3-0.6 mol/L of salt was used for elution, so as to elute the protein from the hydrophobic chromatography column. A solution of the eluted protein was collected.

Desalination chromatography. A desalination chromatography column was equilibrated with an equilibration buffer containing 0.02-0.06 mol/L of salt. The solution of the eluted protein collected from hydrophobic chromatography was loaded on the desalination chromatography column for desalination. A solution of the desalted protein was collected, and then subjected to virus removal nanofiltration and ultrafiltration concentration to obtain a stock solution of the target protein.

Example 2 Discovery and Identification of T100 in Aflibercept Sample

Discovery of T100 in Aflibercept Sample

The sequence and structure of aflibercept prepared in Example 1 are shown in FIG. 1.

The sample prepared in Example 1 was subjected to a molecular weight analysis of IdeS-cleaved non-reducing subunits. As aflibercept contained five N-glycosylation modification sites, the heterogeneity caused by N-glycosylation was very severe and thus aflibercept could not be determined without N-saccharide chain cleavage. Therefore, the N-saccharide cleavage treatment with PNGase F was performed before the subunit molecular weight analysis. The steps of the molecular weight analysis of the IdeS-cleaved non-reducing subunits were as follows.

A 50 μg of sample was diluted to 2 μg/L by adding the IdeS enzyme cleavage buffer (a solution of 50 mM phosphate and 150 mM NaCl, pH 6.6). IdeS was added at a ratio of protein:enzyme=20:1 (mass ratio) and incubated at 37° C. for 1 h.

A 20 μg of IdeS-cleaved sample was added with 4 μl of 5×Reaction buffer (non-reducing buffer), balanced up to a volume of 20 μl with water, and incubated at 75° C. for 5 min. After the end of the incubation, 2 μl of a rapid saccharide-cleaving enzyme Rapid PNGase F (Non-reduction) was added, and mixed to uniformity. Then enzymatic cleavage was performed at 50° C. for 30 min.

After the enzymatic cleavage, centrifugation was performed at 12000 rpm for 3 min, and the supernatant was transferred to a sample vial.

The sample to be tested was subjected to a subunit molecular weight analysis by liquid chromatography-mass spectrometry (LC-MS) using the following conditions for chromatography and mass spectrometry.

Conditions for Chromatography:

| | |
|---|---|
| LC system | ACQUITY I-Class, Waters |
| Chromatography column | Bioresolve RP mAb Polyphenyl, 450 Å, 2.1 × 150 mm |
| Column temperature | 80° C. |
| Sample chamber temperature | 8° C. |
| Mobile phase | A: a solution of 0.1% formic acid/water; B: a solution of 0.1% formic acid/acetonitrile |
| Elution gradient | Phase B increased linearly from 10% to 30% in 8 min and then linearly to 42% in 6 min |

Conditions for Mass Spectrometry:

| | |
|---|---|
| MS system | Xevo G2-XS QTof, Waters |
| Ionization mode | ESI positive |
| Scan range of the first-order mass spectrometry | 500-4000 m/z |
| Capillary voltage | 2.7 kV |
| Cone voltage | 60 V |
| Ion source temperature | 120° C. |
| Desolvation gas temperature | 400° C. |
| Cone gas flow rate | 50 L/h |
| Desolvation gas flow rate | 800 L/h |

Figure 2:
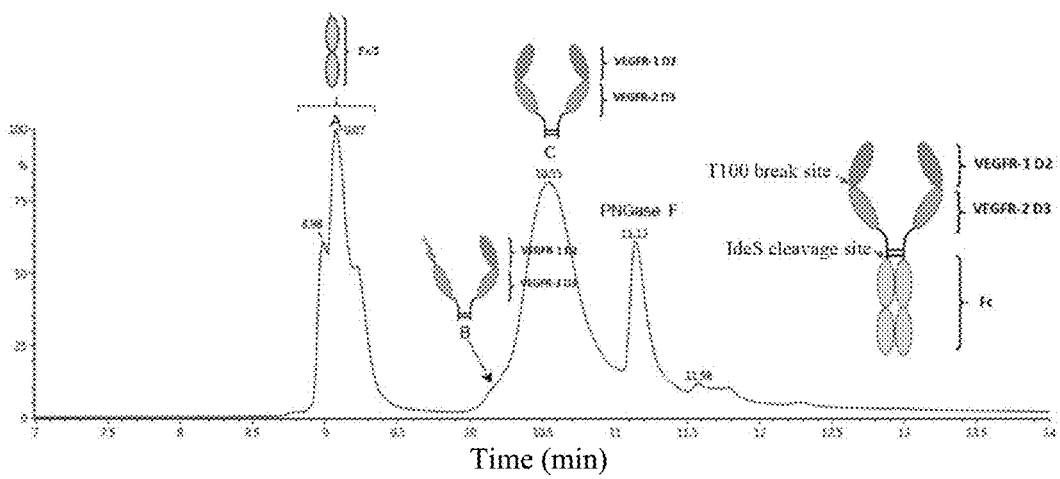
FIG. 2 shows a TIC spectrum of a molecular weight analysis of IdeS-cleaved non-reducing subunits.
Figure 3:
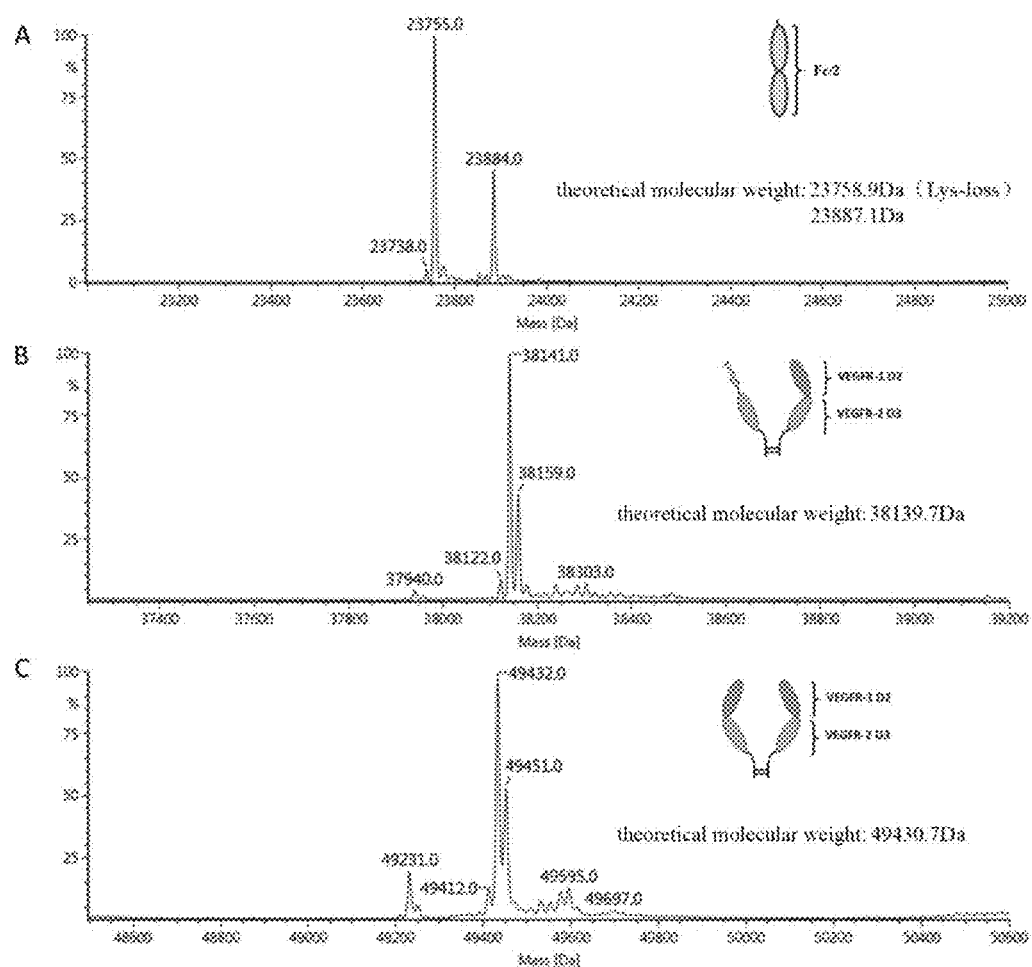
FIG. 3 shows deconvolution spectra of peak A (panel A), peak B (panel B) and peak C (panel C) in the TIC spectrum of the molecular weight analysis of IdeS-cleaved non-reducing subunits, where Lys-loss labeled in panel A is a C-terminal lysine deletion, which is a common post-translational modification of an antibody.

Data processing was performed by using UNIFI 1.8 software from Waters. The total ion chromatogram (TIC) of the molecular weight analysis of IdeS-cleaved non-reducing subunits was shown in FIG. 2, and the deconvolution spectra of main components were shown in FIG. 3.

After enzymatic cleavage of the sample with IdeS, a break occurred downstream of the hinge region to form Fc/2 and VEGFR regions. Results of the molecular weight analysis of non-reducing subunits showed that the peak at 9.07 min (peak A) in the TIC spectrum was Fc/2, and the peak at 10.55 min was the VEGFR region (peak C). The error between the observed molecular weight after deconvolution and the theoretical molecular weight was less than 5.0 Da, indicating that the main components after the IdeS cleavage can be detected. Peak C was preceded by a shoulder (peak B), and the main component after deconvolution was found to have an observed molecular weight of 38141.0 Da. The retention time of peak B was close to that of peak C, and its molecular weight was about 11000 Da less than that of peak C, presumably related to the truncation of the VEGFR region. Upon analysis with reference to the sequence of aflibercept, after N-terminal S1-N99 was truncated from the VEGFR region of one chain, the theoretical molecular weight of the remaining component was 38139.7 Da, similar to the observed molecular weight of peak B.

Identification of T100 in Aflibercept Sample

To confirm the break site, the sample prepared in Example 1 was subjected to a peptide mass fingerprinting analysis. The analytical method had the following steps.

About 40 μg of sample was added with a final concentration of 6M of urea and 10 mM of TCEP, and incubated at 37° C. for 60 min for reduction under a denaturing condition.

IAM at a final concentration of 20 mM was added and incubated for 15 min at 37° C. for alkylation to block free thiol groups.

Urea was diluted to a concentration of 1 M by the addition of 50 mM ammonium bicarbonate buffer. Trypsin was added at a ratio of protein:enzyme=20:1 (mass ratio) and enzymatic cleavage was performed at 37° C. for 25 min.

After the enzymatic cleavage, formic acid was added at the final concentration of 10 to stop the enzymatic cleavage. Centrifugation was performed at 12000 rpm for 3 min, and the supernatant was transferred to a sample vial.

Peptide mass fingerprinting analysis was performed on the sample to be tested by liquid chromatography-tandem mass spectrometry (LC-MS/MS) using the following conditions for chromatography and mass spectrometry.

Conditions for Chromatography:

| | |
|---|---|
| LC system | Vanquish, Thermo |
| Chromatography column | Acquity UPLC Peptide BEH C18 Column, 130 Å, 1.7 μm, 2.1 mm × 100 mm |
| Column temperature | 60° C. |
| Sample chamber temperature | 8° C. |
| Mobile phase | A: a solution of 0.1% formic acid/water; B: a solution of 0.08% formic acid/80% acetonitrile/20% water |
| Elution gradient | After 1% phase B was used for equilibration for 3 min, phase B increased linearly to 45% in 57 min |

Conditions for Mass Spectrometry:

| | |
|---|---|
| MS system | Q-Exactive Plus, Thermo |
| Ionization mode | ESI positive |
| Scan range of the first-order mass spectrometry | 200-2000 m/z |
| Capillary voltage | 3.2 kV |
| Capillary Temp | 320° C. |
| Resolution of the first-order mass spectrometry | 70000 |
| AGC Target | $1e^6$ |
| Resolution of the second-order mass spectrometry | 17500 |
| AGC Target | $1e^5$ |
| Isolation window | 1.6 m/z |

Figure 4:
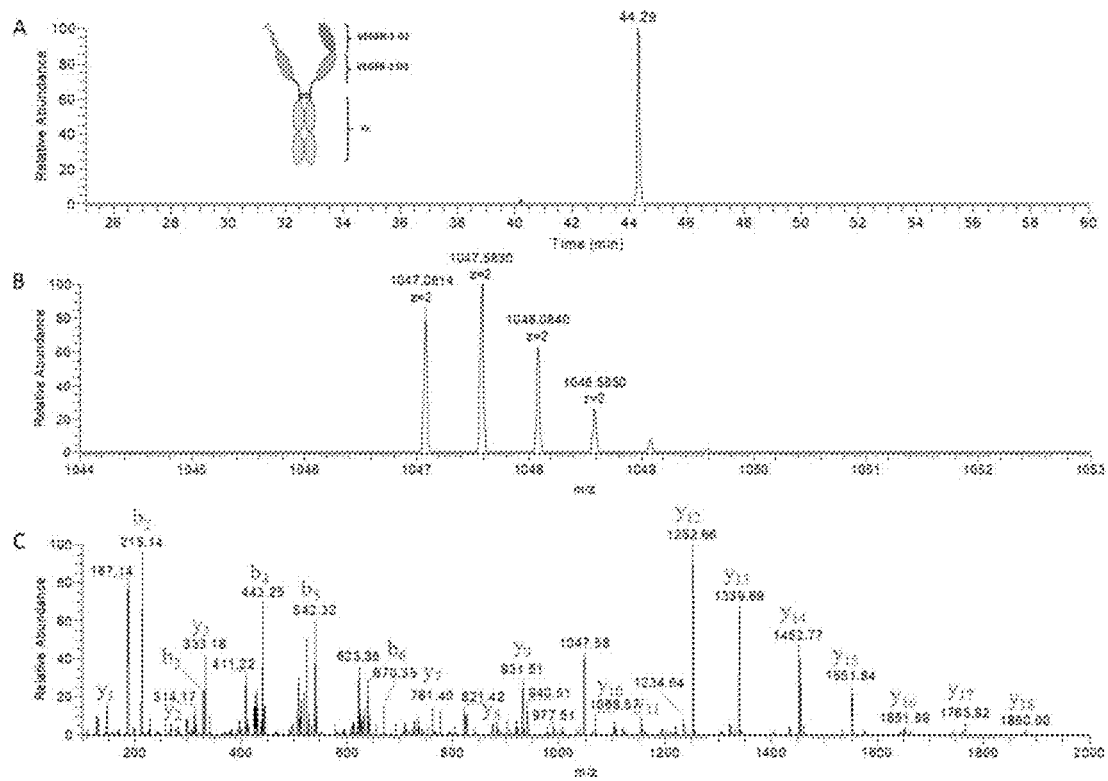
FIG. 4 shows extracted ion chromatogram of the first-order mass spectrometry (panel A), first-order mass spectrum (panel B) and second-order mass spectrum (panel C) of a truncated peptide segment of T100 in an aflibercept sample.

Data processing was performed by pFind software. The extracted ion chromatogram (XIC) of the first-order mass spectrometry, and the first-order and second-order mass spectra of the truncated peptide fragment were shown in FIG. 4.

The results of the peptide mass fingerprinting demonstrate that a truncated peptide segment TIIDVVLSP-SHGIELSVGEK (deleted amino acid residues were indicated by strikeout) was found at the retention time of 44.3 min in the sample. The observed m/z of the monoisotopic peak of the peptide fragment was 1047.0814, the theoretical m/z was 1047.0781, and the error was only 3.15 ppm. Furthermore, ions of the fragment in the second-order mass spectrum can be well matched with the theoretical b and y ions of the peptide fragment, thereby confirming the amino acid sequence of the peptide fragment.

Aflibercept is a homodimer formed from two identical peptide chains linked by disulfide bonds. With reference to the molecular weight analysis results of IdeS-cleaved subunits, peak B was formed by the deletion of S1-N99 sequence from the VEGFR region due to the breakage of the C-terminal peptide chain at position N99 of one peptide chain. The observed molecular weight of peak B was 38141.0 Da. After the N-terminal S1-N99 was truncated from the VEGFR region of one chain, the theoretical molecular weight of the remaining component was 38139.7 Da, further demonstrating that the break site was the N99 site of one peptide chain.

Example 3 The Content of T100 in Aflibercept Sample

Peptide mass fingerprinting analysis was performed on six batches of samples prepared in Example 1 by LC-MS/MS. After the mass spectrometry data was obtained, XIC chromatograms s of two charge forms which had the strongest responses to the truncated peptide segment TIIDVVLSP-SHGIELSVGEK and its corresponding full-length peptide segment QTNTIIDVVLSPSHGIELSVGEK were extracted, and integrated to obtain respective peak areas. The content of T100 was calculated according to the following formula:

$$\text{The content of } T100 = \frac{\text{XIC area of truncated peptide segment}}{\text{XIC area of truncated peptide segment} + \text{XIC area of full-length peptide segment}} \times 100\%$$

The method for sample pre-processing and the method for LC-MS/MS detection were set forth in Example 2. Data processing was performed by using Qualbrowser in the Xcalibur software.

Figure 5:
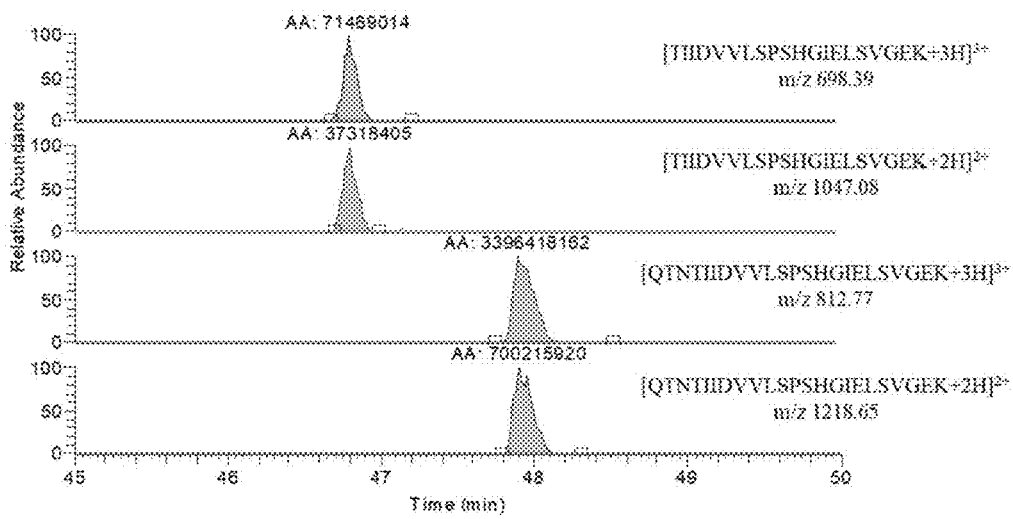
FIG. 5 shows the extracted ion chromatograms of truncated and full-length peptide segments in an aflibercept sample.

Taking the mass spectrometry data of the sample of batch 1 as an example, XIC chromatograms of the truncated peptide segment and the full-length peptide segment were shown in FIG. 5.

The content of T100 in the sample of batch 1 was calculated to be 2.59% according to the following formula:

$$\text{The content of } T100 = \frac{(71469014 + 37318405)}{(71469014 + 37318405) + (3396418162 + 700215920)}$$

The contents of T100 in the samples of various batches were calculated in the same manner. The results were shown in Table 1.

TABLE 1

The contents of T100 in the samples of various batches

| Batch No. | The content of T100 (%) |
|---|---|
| Batch 1 | 2.59 |
| Batch 2 | 0.91 |
| Batch 3 | 0.93 |
| Batch 4 | 0.92 |
| Batch 5 | 0.86 |
| Batch 6 | 2.00 |

The results showed that the contents of T100 in the samples prepared in Example 1 were 0.86%-2.59%.

Example 4 Mass Range of T100 in Aflibercept

A comparative study of binding activity and biological activity was performed between the samples prepared in Example 1 and commercially available Eylea™

The binding ability of various samples to $VEGF_{165}$ protein was determined by ELISA. The assay was as follows: diluting human $VEGF_{165}$ protein to 0.15 μg/ml with a coating solution (50 mM $NaHCO_3$-$Na_2CO_3$, pH9.6), adding 100 μl to each well in a 96-well plate and coating at 2-8° C. overnight;

blocking with 2% BSA-PBS for 2 hours, then adding 100 μl of the sample diluted with 1% BSA-PBST gradient to each well, and incubating at 37° C. for 2 hours;

adding an HRP-labeled goat anti-human IgG Fc antibody to the 96-well plate;

washing thoroughly with PBST between the above steps; and lastly, adding a TMB development solution and a stop solution (2M $H_2SO_4$), reading absorbance at 450 nm by a microplate reader (SPARK multifunctional microplate reader from TECAN). With protein concentration on the X-axis and absorbance on the Y-axis, a curve was fitted by a four-parameter method to obtain calculation results.

The $VEGF_{165}$ binding activities of the samples prepared in six batches in Example 1 and the commercially available Eylea™ were determined, with the sample of batch 6 prepared in Example 1 as a reference control (100%). Results were shown in Table 2.

TABLE 2

Results of $VEGF_{165}$ binding activities of samples of various batches and commercially available Eylea ™

| Samples | Batch No. | $VEGF_{165}$ binding activity (%) |
|---|---|---|
| Commercially available Eylea ™ | KT03612 | 98 |
| | KT0434T | 102 |
| | KT0434V | 87 |
| Aflibercept prepared in Example 1 | Batch 1 | 100 |
| | Batch 2 | 101 |
| | Batch 3 | 100 |
| | Batch 4 | 99 |
| | Batch 5 | 96 |
| | Batch 6 | 100 (control) |

The results showed that the $VEGF_{165}$ binding activities of samples of various batches and commercially available Eylea™ were 80%-120% of the activity of the control. As the precision of the assay for binding activity detection was generally ≤20%, the measured binding activities of 80%-120% relative to the control activity were within the assay fluctuation, indicating that there was no difference in the $VEGF_{165}$ binding activities between the aflibercept samples prepared in Example 1 and commercially available Eylea™.

Biological activities of the various samples were determined using the VEGF activity neutralization-HUVEC cell proliferation inhibition method. Detection of biological activity by this method was based on the following principle. Proliferation of human umbilical vein endothelial cells (HUVEC) can be stimulated by VEGF, and binding of VEGFR:Fc fusion protein to VEGF can neutralize the activity of VEGF, which in turn inhibits the proliferation of HUVEC cells.

First, the samples were diluted with a gradient of assay media while the VEGF protein was diluted to 210 ng/ml. The VEGF protein diluent and the diluted samples from the concentration gradient were sequentially added to a 96-well cell culture plate at 50 l/well, mixed homogeneously in equal volumes and co-incubated for 50-80 minutes.

HUVEC cell density was adjusted to $1.6 \times 10^5$~$2.4 \times 10^5$ cells/ml with the assay medium, added to a 96-well cell culture plate at 50 μl/well, and incubated in a 5% $CO_2$ incubator at 37° C. for 65-70 hours.

After the end of the incubation, the 96-well plate was taken out. 30 μl of Alamar Blue staining solution was added to each well and incubated in an incubator at 37° C. for 6 hours. Data was acquired by a fluorescence microplate reader (SpectraMax Gemini EM from Molecular Devices) at an excitation wavelength of 530 nm and an emission wavelength of 590 nm. With protein concentration on the X-axis and absorbance on the Y-axis, a curve was fitted by a four-parameter method to obtain calculation results.

The biological activities of the samples in six batches prepared in Example 1 and the commercially available Eylea™ were determined, with the sample of batch 6 prepared in Example 1 as a reference control (100%). The results were shown in Table 3.

TABLE 3

Results of biological activities of samples of various batches and commercially available Eylea ™

| Samples | Batch No. | Biological activity (%) |
|---|---|---|
| Commercially available Eylea ™ | KT03612 | 99 |
| | KT0434T | 102 |
| | KT0434V | 107 |
| Aflibercept prepared in Example 1 | Batch 1 | 101 |
| | Batch 2 | 101 |
| | Batch 3 | 96 |
| | Batch 4 | 101 |
| | Batch 5 | 98 |
| | Batch 6 | 100 (control) |

The results showed that the biological activities of the samples of various batches and commercially available Eylea™ were 70%-130% of the activity of the control. As the assay precision of the cell experimentation was generally ≤30%, the measured biological activities of 70%-130% relative to the control activity were within the assay fluctuation, indicating that there was no difference in the biological activities between the aflibercept samples prepared in Example 1 and commercially available Eylea™.

The above results demonstrate that the aflibercept samples prepared in Example 1 were equivalent to commercially available Eylea™ in terms of binding activity and biological activity.

Recombinant expression of TWO was performed according to the results of identification. If the wild-type Fc sequence was used for expression, it was expected that a protein sample of three mixed components would occur: a component with truncations of both chains, a component with a truncation of a single chain (target component), and a component with no truncation of both chains. To obtain a purer component with a truncation of a single chain, the Knob-into-hole design was used for the recombinant expression of T100. Sequence information was shown in Table 4.

TABLE 4

Sequence of T100 for recombinant expression

| | Sequence |
|---|---|
| Chain 1 | SDTGRPFVEMYSEIPEIIHMTEGRELVIPCRVTSPNITV<br>TLKKFPLDTLIPDGKRIIWDSRKGFIISNATYKEIGLLT<br>CEATVNGHLYKTNYLTHRQTNTIIDVVLSPSHGIELSVG<br>EKLVLNCTARTELNVGIDFNWEYPSSKHQHKKLVNRDLK<br>TQSGSEMKKFLSTLTIDGVTRSDQGLYTCAASSGLMTKK<br>NSTFVRVHEKDKTHTCPPCPAPELLGGPSVFLFPPKPKD<br>TLMISRTPEVTCVVVDVSHEDPEVKFNWYVDGVEVHNAK<br>TKPREEQYNSTYRVVSVLTVLHQDWLNGKEYKCKVSNKA<br>LPAPIEKTISKAKGQPREPQVYTLPPCRDELTKNQVSLW |

TABLE 4-continued

Sequence of T100 for recombinant expression

| | Sequence |
|---|---|
| | CLVKGFYPSDIAVEWESNGQPENNYKTTPPVLDSDGSFF<br>LYSKLTVDKSRWQQGNVFSCSVMHEALHNHYTQKSLSLS<br>PGK |
| Chain 2 | TIIDVVLSPSHGIELSVGEKLVLNCTARTELNVGIDFNW<br>EYPSSKHQHKKLVNRDLKTQSGSEMKKFLSTLTIDGVTR<br>SDQGLYTCAASSGLMTKKNSTFVRVHEKDKTHTCPPCPA<br>PELLGGPSVFLFPPKPKDTLMISRTPEVTCVVVDVSHED<br>PEVKFNWYVDGVEVHNAKTKPREEQYNSTYRVVSVLTVL<br>HQDWLNGKEYKCKVSNKALPAPIEKTISKAKGQPREPQV<br>CTLPP*S*RDELTKNQVSL*S*CAVKGFYPSDIAVEWESNGQP<br>ENNYKTTPPVLDSDGSFFL*V*SKLTVDKSRWQQGNVFSCS<br>VMHEALHN*R*YTQKSLSLSPGK |

Note:
the residues shown in italics are mutated amino acids.

The plasmid was transfected into ExpiCHO-S cells by transient electroporation. The cells were cultured in a commercial medium according to an established culture process. After 10 days, the culture was harvested, filtered with a filtration membrane of 0.22 μm pore size, and then subjected to Protein A affinity chromatography, so as to obtain the desired T100.

The purity of main peak in SEC of the transiently expressed T100 sample was 98.9%. The molecular weight analysis of intact molecule after N-saccharide cleavage showed that the observed molecular weight was consistent with the theoretical one.

A T100 gradient was prepared and added to the samples prepared in Example 1. Each sample was detected for the content of T100, and the binding capacity to $VEGF_{165}$ protein and biological activity.

The contents of T100 and activities of the various samples were shown in Table 5.

TABLE 5

The contents of T100 and activities of the various samples

| Sample name | T100 content (%) | Binding activity (%) [1,2] | Biological Activity (%) [1,2] |
|---|---|---|---|
| Added sample 1 | 6.22 | 96 | 92 |
| Added sample 2 | 9.68 | 95 | 95 |
| Added sample 3 | 12.51 | 87 | 88 |
| Added sample 4 | 16.19 | 84 | 83 |
| Added sample 5 | 19.29 | 80 | 75 |
| Added sample 6 | 23.63 | 73 | 69 |

Note:
[1] The sample of batch 1 prepared in Example 1 was a reference control (100%).
[2] The results of the binding activity and biological activity were the averages from three assays.

The results showed that the binding activity and the biological activity of the aflibercept samples decreased gradually with the increase of the content of T100. Therefore, the content of T100 needed to be controlled during the preparation of aflibercept.

Various changes and equivalent substitutions can be made to the embodiments disclosed herein without departing from the spirit and scope of the disclosure. Unless otherwise indicated in the context, any feature, step, or embodiment of the disclosed embodiments can be used in combination with any other features or embodiments.

---

What is claimed is:

1. A composition comprising aflibercept and a variant thereof, wherein the variant is a truncation variant with a truncated VEGF binding portion of aflibercept, and said variant comprises a first peptide chain with an amino acid sequence set forth in SEQ ID NO: 1 and a second peptide chain with an amino acid sequence set forth in SEQ ID NO: 2, and wherein the content of the truncation variant in the composition is less than or equal to about 20% by mass percentage, which is calculated based on a trypsin-cleaved peptide mass fingerprinting analysis.

2. The composition of claim 1, wherein the content of aflibercept in the composition is greater than or equal to about 80% by mass percentage.

3. The composition of claim 1, wherein the content of the truncation variant is greater than or equal to about 0.5%.

4. The composition of claim 1, wherein the content of the truncation variant is less than or equal to about 19%.

5. A pharmaceutical formulation comprising the composition of claim 1, and one or more pharmaceutically acceptable carriers.

* * * * *